US008822670B2

(12) United States Patent
Kinoshita et al.

(10) Patent No.: US 8,822,670 B2
(45) Date of Patent: Sep. 2, 2014

(54) METHOD OF SYNTHESIZING CDNA AND METHOD OF SYNTHESIZING RNA CHAINS, AND NUCLEOTIDE-IMMOBILIZED CARRIER

(75) Inventors: Kenji Kinoshita, Hyogo (JP); Toru Yakabe, Tokyo (JP); Kentaro Fujimoto, Tokyo (JP); Kanehisa Yokoyama, Tokyo (JP); Kazuhiko Fujiwara, Tokyo (JP)

(73) Assignees: Sumitomo Bakelite Company, Ltd., Tokyo (JP); Kenji Kinoshita, Hyogo (JP)

( * ) Notice: Subject to any disclaimer, the term of this patent is extended or adjusted under 35 U.S.C. 154(b) by 1349 days.

(21) Appl. No.: 11/990,641

(22) PCT Filed: Aug. 9, 2006

(86) PCT No.: PCT/JP2006/315734
§ 371 (c)(1),
(2), (4) Date: Feb. 19, 2008

(87) PCT Pub. No.: WO2007/020847
PCT Pub. Date: Feb. 22, 2007

(65) Prior Publication Data
US 2010/0016566 A1    Jan. 21, 2010

(30) Foreign Application Priority Data
Aug. 19, 2005    (JP) ................. P2005-238591

(51) Int. Cl.
*C07H 21/00*    (2006.01)
(52) U.S. Cl.
USPC ........................................ 536/25.3; 536/23.1
(58) Field of Classification Search
USPC ................ 435/6.1, 6.12, 91.2; 536/23.1, 25.3
See application file for complete search history.

(56) References Cited

U.S. PATENT DOCUMENTS

| 5,424,219 | A |   | 6/1995  | Jirikowski |             |
|-----------|---|---|---------|------------|-------------|
| 5,437,976 | A |   | 8/1995  | Utermohlen |             |
| 5,484,701 | A | * | 1/1996  | Cocuzza et al. | 435/6.11 |
| 5,559,001 | A |   | 9/1996  | Utermohlen |             |
| 5,564,104 | A | * | 10/1996 | Pourfarzaneh | 588/20    |
| 5,595,879 | A |   | 1/1997  | Utermohlen |             |
| 5,656,462 | A | * | 8/1997  | Keller et al. | 435/91.2 |
| 5,900,481 | A | * | 5/1999  | Lough et al. | 506/30    |
| 6,485,918 | B1 | * | 11/2002 | Schermer et al. | 506/43 |
| 7,211,414 | B2 | * | 5/2007  | Hardin et al. | 435/91.1 |
| 2005/0079506 | A1 | * | 4/2005 | Leon et al. | 435/6    |

FOREIGN PATENT DOCUMENTS

| EP | 1820857 A1 | 8/2007 |
| JP | 8-500722 | 1/1996 |
| JP | 2003-519482 | * 6/2003 |
| WO | 90/11369 | 10/1990 |
| WO | 93/03052 | 2/1993 |
| WO | 93/04199 | 3/1993 |
| WO | 93/08471 | 4/1993 |
| WO | 93/15228 | 8/1993 |
| WO | 01/51601 | 7/2001 |
| WO | 2004/065573 | 8/2004 |
| WO | 2005/029095 | 3/2005 |

OTHER PUBLICATIONS

Keller (Aug. 5, 1993) PCT International Patent Application Publication WO 93/15228 A1.*
Hunoka (Mar. 31, 2005) PCT International Patent Application Publication WO 2005/029095 A1.*
Lewis (Oct. 2000) Colloids and Surfaces B Biointerfaces vol. 18 pp. 261 to 275.*
Takei et al. (Mar. 10, 2004) Biomacromolecules vol. 5 pp. 858 to 862.*
Supplementary European Search Report for Application No. EP 06 78 2550 dated Mar. 2, 2010.
Giusti et al., "Synthesis and Characterization of 5' Fluorescent-dye-labeled Oligonucleotides", PCR Methods and Applications, Feb. 1993, vol. 2, No. 3, pp. 223-227.
Sano et al., "Comparison of the sensitives of two non-isotopic reverse transcriptase (RT) assays for human immunodeficiency virus type 1 RT", Journal of Virological Methods, Apr. 26, 1996, vol. 58, No. 1-2.
Yolken et al., "Solid phase capture method for the specific amplification of microbial nucleic acids—avoidance of false-positive and false-negative reactions", Molecular and Cellular Probes, Academic Press, London, GB, vol. 5, No. 2, Apr. 1, 1991, pp. 151-156.
I. Raineri et al, "Improved efficiency for single-sided PCR . . . phase", Nucleic Acids Research, vol. 19, No. 14, Jul. 25, 1991, p. 4010.
S. Shichijo et al., "Histamine Effects on the . . . Oocytes", Journal of Neuroscience Research, vol. 30, No. 2, Oct. 1991, pp. 316-320.
Stamm et al., "Sanchored PCR: PCR with CDNA . . . phase", Nucleic Acids Research, vol. 19, No. 6, Mar. 25, 1991, p. 1350.
U.S. Appl. No. 10/572,332, filed Sep. 17, 2004, Ishihara et al.
European Patent Office Communication received in EP Application Serial No. 06782 550.5, mailed Mar. 17, 2011.
Park, J. et al. (2004) "Evaluation of 2-Methacryloyloxyethyl Phosphorylcholine Polymeric Nanoparticle for Immunoassay of C-Reactive Protein Detection" Analytical Chemistry, 76:2649-2655.

(Continued)

*Primary Examiner* — Ardin Marschel
(74) *Attorney, Agent, or Firm* — Smith, Gambrell & Russell LLP

(57) ABSTRACT

A method of synthesizing a cDNA chain using an insoluble carrier having on the surface thereof a polymer substance containing a first unit having a group derived from a phosphoric ester composing the hydrophilic portion of phospholipid, and a second unit having a group derived from carboxylic acid having an electron-attractive substituent bound to a carbonyl group, which includes immobilizing a polynucleotide for DNA elongation; bringing a solution containing an RNA fragment, nucleotide monomers, and a reverse transcriptase or an enzyme having polymerase activity into contact with the surface of the insoluble carrier; and allowing the polynucleotide for DNA elongation immobilized on the surface of the carrier to elongate using the RNA fragment contained in the solution as a template, to thereby form a single-strand cDNA.

9 Claims, No Drawings

(56) References Cited

OTHER PUBLICATIONS

Konno, T. et al. (2004) "Conjugation of Enzymes on Polymer Nanoparticles Covered with Phosphorycholine Groups" Biomacromolecules, 5:342-347.

Kinoshita, K. et al. (2006) "Multiple Primer Extension by DNA Polymerase on a Novel Pplastic DNA Array Coated with a Biocompatible Polymer" Nucleic Acids Research, 35. Published Online.

Tanaka, A. et al. (2009) "All-in-one Tube Method for Quantitative Gene Expression Analysis in Oligo-dT30 Immobilized PCR Tube Coated with MPC Polymer" Analytical Sciences, 25:109-114.

Hinori Torada (1991) "Ketei ka DNA niyeru Tensha . . ." Biophysics, the Biophysical Society of Japan, 31:6.

* cited by examiner

METHOD OF SYNTHESIZING CDNA AND METHOD OF SYNTHESIZING RNA CHAINS, AND NUCLEOTIDE-IMMOBILIZED CARRIER

TECHNICAL FIELD

The present invention relates to a polynucleotide-immobilized carrier useful for preservation and analysis of gene, a method of synthesizing a cDNA using the polynucleotide-immobilized carrier, and a method of synthesizing a DNA chain and an RNA chain using the cDNA as a template.

BACKGROUND ART

Most lives keeps their genetic information in a form of DNA. The DNA is transcribed to messenger RNA (mRNA), and the mRNA is further translated to protein. In eukaryotic cells, some deletion of genetic information generally occur, when the DNA is processed to synthesize a matured mRNA. The deletion is caused by RNA splicing of intoron/exon, or protein processing. It is therefore understood that mRNA may be used for studying basic genetic analysis of protein structure, more advantageously than genomic DNA.

The mRNA is, however, very unstable, and may readily be decomposed by various ribonucleases. For this reason, DNA chain (cDNA) synthesized based on mRNA has been used as a material for the study. The cDNA is synthesized by using a target mRNA as a template, with the aid of a reverse transcriptase capable of synthesizing single-strand DNA.

Besides use of a promoter of a vector involved in transcription of mRNA (or, sense mRNA) containing a sequence capable of coding a polypeptide, it is also possible to synthesize an antisense mRNA transcribed from a complementary cDNA chain. The antisense mRNA is a powerful tool for understanding biological functions of proteins, and mRNA whose actions are remained unknown. The antisense RNA molecule can block production of a specific protein by inhibiting transcription, when annealed with a target mRNA. This type of inhibition of transcription is, therefore, supposed to be important for studying various gene products involved in various symptoms.

The single-strand cDNA is useful not only as a starting materials for synthesizing a double-strand cDNA with the aid of catalytic action of a DNA polymerase, but also as a template for polymerase chain reaction (referred to as PCR, hereinafter) According to this method, a specific genetic sequence may rapidly be amplified, using a plurality of nucleotide primers having reverse directionality, and a heat-resistant DNA polymerase. Copies of the target gene may rapidly be produced by repeating a cycle of annealing and DNA synthesis. In this way, the sense single-strand cDNA may be used for specifically amplifying segments of corresponding double-strand cDNA.

In the liquid phase process, thus-synthesized double-strand cDNA contains no marker which determines the directionality of the molecule. Therefore, newly synthesized double-strand cDNA clones are supposed to contain a 50% error in the direction of transcription, and cannot directly be inserted into a cloning vector. For this reason, there has been a demand for a technique of allowing insertion into vector under the correct directionality, and allowing rapid cloning of mRNA.

The single-strand cDNA or the double-strand cDNA may be synthesized also by using a solid phase (Non-Patent Document 1). In the general solid phase process, poly-deoxythymidylic acid (poly-dT) complementarily binds with the tail of polyadenylic acid (polyA) of a mRNA immobilized on a porous bead. Next, an antisense single-strand cDNA is synthesized based on the bound mRNA, with the aid of a reverse transcriptase. After digestive decomposition of the template RNA, a second cDNA chain is synthesized by a DNA polymerase. The synthesized double-strand cDNA has an antisense chain immobilized on the bead.

The solid phase process, however, cannot release the double-strand-cDNA product from the insoluble carrier. To avoid this problem, the double-strand cDNA product is heated so as to release the single-strand cDNA from the double-strand cDNA immobilized on the carrier, and the double-strand cDNA is synthesized by PCR using the single-strand cDNA. This, however, means a need of one additional step for the reaction, and a need of one appropriate set of primers for every PCR reaction.

Therefore, there has been a demand for a simple method of synthesizing a non-binding-type double-strand cDNA from an isolated mRNA.

On the other hand, there are known various methods of synthesizing the mRNA from the cDNA clone, one of which being the liquid phase process (Non-Patent Document 2). In this process, a double-strand cDNA is inserted to a vector having an RNA promoter. The vector is then digested by a restriction enzyme to produce a straight chain, and the mRNA is synthesized by an action of an RNA polymerase. The synthesized mRNA is treated with a DNase for removing the template DNA. If necessary, a polyadenylic acid tail is added in this process to the terminal of the newly-synthesized RNA, using a terminal transferase and dATP.

Also the solid phase synthesis process of mRNA is well known. One of them is described in Non-Patent Document 3. In this process, a DNA sequence is digested from a genome of bacteriophage lambda, to thereby produce a random DNA fragment having a sticky end. The sticky end is then blunted with a biotin-modified dUTP with the aid of T4 DNA polymerase.

In the process of DNA synthesis using T4 DNA polymerase, the restriction enzyme is selected so as to leave a sticky end having an exposed dA nucleotide so as to allow the biotin-modified dUTP to hybridize therewith. The random sequence is then immobilized onto an acrylamide carrier bound with avidin. The mRNA is synthesized from a sequence having a naturally-occurred lambda promoter sequence, using T7 RNA polymerase or SP6 RNA polymerase. This system is designed for the purpose of study based on kinetic analysis of transcription by bacteriophage lambda.

Both processes of liquid-phase and solid-phase syntheses of mRNA have drawbacks. The liquid-phase synthetic process is in need of using the RNA-promoter-containing vector, and the vector after being inserted must be converted into a straight-chain sequence. The solid-phase synthetic process does not always necessarily provide a complete genetic information. This is because the information is that of the immobilized genomic DNA, but not of mRNA. For this reason, there is a demand for an improved method of synthesizing mRNA.

Non-Patent Document 4 describes that an oligonucleotide covalently bound through an amino bond to a solid-phase carrier may conveniently be used for PCR experiment. The technique described in this document, however, does not specifically provide production of cDNA and RNA. Moreover, there is no description on a mechanism of removing the oligonucleotide covalently bound to the carrier.

Non-Patent Document 1 discloses a method by which an oligonucleotide is immobilized on a solid carrier, and cDNA is then synthesized on the solid surface using RNA as a template. Non-Patent Document 2 discloses a method by which RNA is immobilized on a carrier, and cDNA is synthesized using a reverse transcriptase.

The enzymatic elongation function of nucleic acid chain is, however, less likely to proceed between the solid surface and the liquid phase, leaving some problem in that whether the synthesized cDNA exactly reflects a state of expression of mRNA used as a template.

[Non-Patent Document 1] I. Raineri et al., Nucleic Acids Research, 19:4010, 1991
[Non-Patent Document 2] S. Shichijo et al., J. Neurosci. Res., 30:316-320, 1991
[Non-Patent Document 3] Hironori Terada, "Kotei-ka DNA niyoru Tensha no Doteki Kaiseki (Dynamic Analysis of Transcription by Immobilized DNA)", Biophysics, 31:49-52, 1991
[Non-Patent Document 4] Stamm et al., Nucleic Acids Res., 19:1350, 1991
[Patent Document 1] Published Japanese Translation of PCT International Publication for Patent Application No. 8-500722
[Patent Document 2] Published Japanese Translation of PCT International Publication for Patent Application No. 2003-519482

DISCLOSURE OF THE INVENTION

It is therefore an object of the present invention to provide a method of synthesizing cDNA, capable of proceeding the elongation reaction of a DNA chain on an insoluble carrier using mRNA as a template effectively, and of exactly reflecting a state of expression of the template mRNA, and a method of readily synthesizing an RNA chain and a DNA chain based on thus synthesized cDNA.

According to the present invention, there is provided:

(1) a method of synthesizing a cDNA chain using an insoluble carrier having on the surface thereof a polymer substance containing a first unit having a group derived from a phosphoric ester composing the hydrophilic portion of phospholipid, and a second unit having a group derived from carboxylic acid having an electron-attractive substituent bound to a carbonyl group, which includes:

(1) forming a polynucleotide-immobilized carrier by immobilizing to the insoluble carrier a polynucleotide for DNA elongation;

(2) bringing a solution containing an RNA fragment, nucleotide monomers, and a reverse transcriptase or an enzyme having polymerase activity into contact with the surface of the insoluble carrier;

(3) allowing the polynucleotide for DNA elongation immobilized on the surface of the carrier to elongate using the RNA fragment contained in the solution as a template, to thereby form a single-strand cDNA;

(2) a method of synthesizing a cDNA chain using an insoluble carrier having on the surface thereof a polymer substance containing a first unit having a group derived from a phosphoric ester composing the hydrophilic portion of phospholipid, and a second unit having a group derived from carboxylic acid having an electron-attractive substituent bound to a carbonyl group, which includes:

(a) allowing at least one polynucleotide for DNA elongation, containing a sequence complementary to the poly-A tail of an mRNA, to bind to the insoluble carrier;

(b) adding a sample solution containing an mRNA having the poly-A tail, a solution containing a reverse transcriptase, and a solution containing nucleotide monomers, to the carrier having immobilized thereon the nucleotide for DNA elongation;

(c) allowing the poly-A tail of the mRNA to hybridize with the sequence complementary to the poly-A tail; and (d) allowing the polynucleotide for DNA elongation to elongate using the mRNA as a template, to thereby form an antisense cDNA complementary to the mRNA;

(3) the method of synthesizing a cDNA chain described in (2), wherein steps (c) and (d) are allowed to proceed in the same liquid phase;

(4) the method of synthesizing a cDNA chain described in (2) or (3), wherein each of steps (c) and (d) involves incubation at a predetermined temperature;

(5) the method of synthesizing a cDNA chain described in any one of (1) to (4), wherein the group derived from a phosphoric ester contained in the first unit of the polymer substance is at least any one species selected from phosphorylcholine group, phosphoryl ethanolamine group, phosphoryl serine group, phosphoryl inositol group, phosphoryl glycerol group, and phosphatidyl phosphoryl glycerol group;

(6) the method of synthesizing a cDNA chain described in any one of (1) to (5), wherein the solution containing nucleotide monomers contains dATP, dCTP, dGTP and dTTP;

(7) the method of synthesizing a cDNA chain described in any one of (1) to (6), wherein the polynucleotide for DNA elongation further contains at least one RNA promoter;

(8) a single-strand cDNA-immobilized carrier obtained by removing the liquid phase from the carrier, having immobilized thereon the single-strand cDNA chain, synthesized by the method of synthesizing a cDNA chain described in any one of (1) to (7);

(9) a method of synthesizing a DNA chain using the single-strand cDNA-immobilized carrier described in (8), which includes bringing a solution containing sense and antisense primers, a DNA polymerase, and nucleotide monomers into contact with the carrier, and allowing PCR to proceed under a predetermined heat cycle, to thereby elongate and amplify the a DNA chain using the single-strand cDNA immobilized on the carrier as a template to synthesize a DNA chain in a liquid phase;

(10) the method of synthesizing a DNA chain described in (9), wherein the nucleotide monomers contain dATP, dCTP, dGTP and dTTP, at least one of which being labeled;

(11) a method of synthesizing a DNA chain, which includes bringing a solution containing a DNA polymerase, a DNA ligase and nucleotide monomers into contact with the surface of a cDNA-immobilized carrier additionally containing an RNA promoter, the carrier being manufactured as having a single-strand cDNA immobilized thereon by the method of synthesizing a cDNA chain described in (7), followed by removal of the liquid phase to form a double-strand cDNA chain;

(12) the method of synthesizing a DNA chain described in (11), wherein the nucleotide monomers contain dATP, dCTP, dGTP and dTTP, at least one of which being labeled;

(13) a method of synthesizing a sense RNA chain, which includes bringing a solution containing an RNA polymerase and nucleotide monomers into contact with the surface of a double-strand cDNA-immobilized carrier additionally containing an RNA promoter, the carrier being manufactured as having a double-strand cDNA immobilized thereon by the method of synthesizing a DNA chain described in (11), and then followed by removal of the liquid phase to synthesize an RNA chain;

(14) the method of synthesizing a sense RNA chain described in (13), wherein the nucleotide monomers contain ATP, CTP, GTP and UTP, at least one of which being labeled;

(15) a nucleotide-immobilized insoluble carrier having, as being immobilized on an insoluble carrier, a polynucleotide containing at least one sequence complementary to the poly-A tail of an mRNA, the insoluble carrier having on the surface thereof a polymer substance containing a first unit having a group derived from a phosphoric ester composing the hydrophilic portion of phospholipid, and a second unit having a group derived from carboxylic acid having an electron-attractive substituent bound to a carbonyl group;

(16) the nucleotide-immobilized carrier described in (15), wherein the immobilized nucleotide further contains at least one RNA promoter;

(17) the nucleotide-immobilized carrier described in (15), wherein the group derived from a phosphoric ester contained in the first unit of the polymer substance is at least any one group selected from phosphorylcholine group, phosphoryl ethanolamine group, phosphoryl serine group, phosphoryl inositol group, phosphoryl glycerol group, and phosphatidyl phosphoryl glycerol group;

(18) the nucleotide-immobilized carrier described in (15) or (16), wherein the polynucleotide contains a nucleotide having 6 to 100 bases;

(19) the nucleotide-immobilized carrier described in any one of (15) to (18), wherein forms of the insoluble carrier include a microtiter plate;

(20) the nucleotide-immobilized carrier described in (19), wherein the microtiter plate has at least two wells, and each of the wells contains an immobilized polynucleotide differing from each other;

(21) the nucleotide-immobilized carrier described in any one of (16) to (20), wherein the polynucleotide contains T7 RNA promoter or SP6 RNA promoter;

(22) the nucleotide-immobilized carrier described in any one of (15) to (21), wherein the polynucleotide contains poly-dT as a sequence complementary to the poly-A tail of the mRNA;

(23) the nucleotide-immobilized carrier described in any one of (15) to (22), wherein the polynucleotide contains at least two RNA promoters;

(24) the nucleotide-immobilized carrier described in (23), wherein the polynucleotide contains at least two RNA promoters different from each other;

(25) the nucleotide-immobilized carrier described in (23) or (24), wherein the polynucleotide contains T7 RNA promoter and SP6 RNA promoter;

(26) the nucleotide-immobilized carrier described in any one of (15) to (25), wherein the polymer substance has a third unit containing butyl methacrylate group;

(27) the nucleotide-immobilized carrier described in any one of (15) to (26), wherein the insoluble carrier contains, in addition to the polymer substance, a second polymer substance having a first unit containing phosphorylcholine group, and a third unit containing butyl methacrylate group, in the surficial portion thereof;

(28) the nucleotide-immobilized carrier described in any one of (15) to (27), wherein the insoluble carrier is composed of a plastic material;

(29) the nucleotide-immobilized carrier described in (28), wherein the plastic material is such as having a glass transition point of 100° C. or above; and

(30) the nucleotide-immobilized carrier described in (28), wherein the plastic material is a saturated cyclic saturated cyclic polyolefin resin.

The present invention can provide a method of synthesizing cDNA, capable of proceeding the elongation reaction of DNA chain on an insoluble carrier using RNA as a template in an efficient manner, capable of exactly reflecting a state of expression of the template mRNA, capable of storing cDNA in a stable manner, and capable of readily synthesizing an RNA chain and a DNA chain based on thus stored cDNA.

BEST MODES FOR CARRYING OUT THE INVENTION

Paragraphs below will detail embodiments of the present invention.

First Embodiment

The present invention provides a method of synthesizing a cDNA chain using an insoluble carrier having on the surface thereof a polymer substance containing a first unit having a group derived from a phosphoric ester composing the hydrophilic portion of phospholipid, and a second unit having a group derived from carboxylic acid having an electron-attractive substituent bound to a carbonyl group, which includes:

(1) forming a polynucleotide-immobilized carrier by immobilizing to the insoluble carrier a polynucleotide for DNA elongation;

(2) bringing a solution containing an RNA fragment, nucleotide monomers, and a reverse transcriptase or an enzyme having polymerase activity into contact with the surface of the insoluble carrier;

(3) allowing the polynucleotide for DNA elongation immobilized on the surface of the carrier to elongate using the RNA fragment contained in the solution as a template, to thereby form a single-strand cDNA.

First, (1) a polynucleotide-immobilized carrier is formed by immobilizing a polynucleotide for DNA elongation, as a primer, on the surface of an insoluble carrier.

The carrier used herein is designed to have, as residing on the surface thereof, a polymer substance containing a first unit having a group derived from a phosphoric ester composing the hydrophilic portion of phospholipid, represented by phosphorylcholine group, and a second unit having a group derived from carboxylic acid.

The polymer substance containing a first unit having a group derived from a phosphoric ester composing the hydrophilic portion of phospholipid, represented by a phosphorylcholine group, and a second unit having a group derived from carboxylic acid, is a polymer having both properties of suppressing non-specific adsorption of RNA chain and of immobilizing a DNA chain. In particular, the phosphoric ester group composing the hydrophilic portion of phospholipid represented by phosphorylcholine group, contained in the first unit, plays a role of suppressing non-specific adsorption of a template RNA fragment, and the group derived from carboxylic acid, contained in the second unit, plays a role of chemically immobilizing a primer. More specifically, the primer is immobilized onto the surface of the carrier, through a covalent bond at the site of an active ester group in the coated layer.

The group derived from a phosphoric ester contained in the first unit may be exemplified by phosphorylcholine group, phosphoryl ethanolamine group, phosphoryl serine group, phosphorylinositol group, phosphoryl glycerol group, and phosphatidyl phosphoryl glycerol group, wherein phosphorylcholine group is particularly preferable. The phosphorylcholine group may be exemplified by (meth)acryloyloxyalkyl phosphorylcholine groups such as 2-methacryloyloxyethyl phosphorylcholine group, and 6-methacryloyloxyhexyl phosphorylcholine group; (meth)acryloyloxyalkoxyalkyl phosphorylcholine groups such as 2-methacryloyloxyethoxyethyl phosphorylcholine group, and 10-methacryloyloxyethoxynonyl phosphorylcholine group; and alkenyl phosphorylcholine groups such as allylphosphorylcholine group, butenyl phosphorylcholine group, hexenyl phosphorylcholine group, octenyl phosphorylcholine group, and decenyl phosphorylcholine group.

Of these phosphorylcholine groups, 2-methacryloyloxyethyl phosphorylcholine is preferable. By composing the first unit as having 2-methacryloyloxyethyl phosphorylcholine, the non-specific adsorption of the template RNA fragment on the surface of the carrier may be suppressed in a more reliable manner.

Although the basic skeleton described herein was exemplified by a phosphorylcholine group expressed by the formula (a) below, the phosphorylcholine may be replaced by phosphoric groups such as phosphoryl ethanolamine group expressed by the formula (b) below, phosphoryl inositol group expressed by the formula (c) below, phosphoryl serine group expressed by the formula (d) below, phosphoryl glycerol group expressed by the formula (e) below, and phosphatidyl phosphoryl glycerol group expressed by the formula (f) below (the same will apply hereinafter).

(Chemical Formula 1)

$$\mathrm{-O-\overset{O}{\underset{OH}{\overset{\|}{P}}}-OCH_2CH_2N^+(CH_3)_3} \quad (a)$$

$$\mathrm{-O-\overset{O}{\underset{OH}{\overset{\|}{P}}}-OCH_2CH_2N^+H_3} \quad (b)$$

(c) phosphoryl inositol structure $$\mathrm{-O-\overset{O}{\underset{OH}{\overset{\|}{P}}}-OCH_2CHCOO^-}\quad (d)$$
with $N^+H_3$ on the CH $$\mathrm{-O-\overset{O}{\underset{OH}{\overset{\|}{P}}}-OCH_2-CHOH-CH_2OH}\quad (e)$$

(f) phosphatidyl phosphoryl glycerol structure

The carboxylic acid derivative is a carboxylic acid activated at the carboxyl group thereof, and having a leaving group bound via C=O. The carboxylic acid derivative is, more specifically, a compound having, as being bound to the carbonyl group, a group having a electron withdrawal property larger than that of alkoxy group, and is thereby made more labile to nucleophilic reaction. The carboxylic acid group is a compound showing reactivity to amino group, thiol group, hydroxyl group and so forth.

The activated carboxylic acid derivative may further specifically be exemplified by compounds having a carboxyl group of carboxylic acid, including acrylic acid, methacrylic acid, crotonic acid, maleic acid, fumaric acid, and so forth, converted to acid anhydride, acid halide, activated ester, and activated amide. Carboxylic acid derived group is an activated group derived from these compounds, and may have, for example, activated ester groups such as p-nitrophenyl group and N-hydroxy succinimide group; and halogen such as —Cl, —F and so forth.

The group derived from carboxylic acid may be a group expressed by the formula (1) below:

(Chemical Formula 2)

$$\mathrm{-\overset{O}{\underset{\|}{C}}-A} \quad (1)$$

(in the formula (1), A represents a leaving group excluding hydroxyl group).

The monovalent group expressed by the formula (1) may be, for example, either group selected from the those expressed by the formulae (p) and (q) below:

(Chemical Formula 3)

$$\mathrm{-\overset{O}{\underset{\|}{C}}-O-CR^1} \quad (p)$$

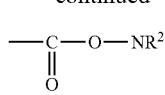

(in the formulae (p) and (q), each of $R^1$ and $R^2$ independently represents a monovalent organic group, and may be any of straight-chain-like, branched and cyclic ones. In the formula (p), $R^1$ may be a divalent group capable of forming a ring in cooperation with C. In the formula (q), $R^2$ may be a divalent group capable of forming a ring in cooperation with N).

Groups expressed by the formula (p) may be exemplified by those expressed by the formulae (r), (s) and (w) below. Groups expressed by the formula (q) may be exemplified by those expressed by the formula (u) below.

The group expressed by the formula (1) may be groups derived from acid anhydride typically expressed by the formula (r) and formula (s) below;

groups derived from acid halide expressed by the formula (t) below;

groups derived from activated ester expressed by the formula (u) and formula (w) below; or groups derived from activated amide expressed by the formula (v) below;

(Chemical Formula 4)

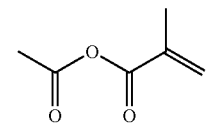

(r)

(s)

(t)

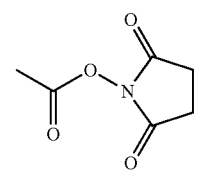

(u)

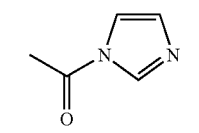

(v)

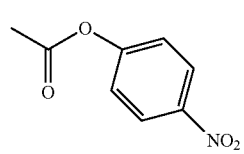

(w)

Of the carboxylic acid-derived groups, the activated ester groups may preferably be used by virtue of their excellent reactivity under mild conditions. The mild conditions may be neutral or alkali conditions, more specifically those with pH7.0 or higher and 10.0 or lower, still more specifically pH7.6 or higher and 9.0 or lower, and furthermore specifically pH8.0.

The "activated ester group" specified in this patent specification is not strictly defined, but is generally used as an idiomatic technical expression in the fields of various chemical syntheses such as polymer chemistry, peptide synthesis and so forth, as indicating a category of esters having, on the alcohol side of the ester group thereof, a highly-acidic, electron-withdrawing group and thereby making the compound more labile to nucleophilic reaction, in other words, highly-reactive ester groups. In the field of peptide synthesis, the active ester process is used as one method of activating the C-terminal of amino acids or peptides, as described in "Pepuchido Gosei no Kiso to Jikken (Basics and Experiments of Peptide Synthesis)", co-written by Nobuo IZUMIYA, Tetsuo KATO, Michihiko AOYAGI and Michinori Waki, 1985, published by Maruzen Co., Ltd.

In practice, it is an ester group having an electron-withdrawing group on the alcohol side of the ester group thereof, and thereby activated to a larger degree than alkyl esters. The activated ester group has reactivity to groups such as amino group, thiol group, and hydroxyl group. More specifically, phenol esters, thiophenol esters, N-hydroxylamine esters, cyanomethyl esters, and esters of heterocyclic hydroxy compounds are known as activated ester groups having far higher activities than those of alkyl esters.

Now the description will be made on the case where the activated carboxylic acid derivative group in the polymer substance is the activated ester group. The activated ester group is exemplified, for example, by p-nitrophenyl group, N-hydroxysuccimide group, succinimide group, phthalimide group, and 5-norbornene-2,3-dicarboxyimide group, wherein p-nitrophenyl group is preferably used.

As for the carrier later having primers immobilized thereon, specific combinations of the first unit and the second unit may be such that the first unit having a phosphorylcholine group has a 2-methacryloyloxyethyl phosphorylcholine group, and the activated ester group is p-nitrophenyl group.

The polymer substance used for a coating layer of the carrier of this embodiment may contain any group other than the phosphorylcholine group and the carboxylic acid-derived group. The polymer substance may also be a copolymer. More specifically, the polymer substance is preferably a copolymer containing butyl methacrylate groups. This configuration can make the polymer substance hydrophobic to an appropriate degree, and can thereby ensure a more preferable level of adsorptivity of the polymer substance to the surface of the carrier.

More specifically, the polymer substance may be configured by a copolymer composed of a first monomer having 2-methacryloyloxyethyl phosphorylcholine (MPC) group, a second monomer having a p-nitrophenyloxycarbonyl polyethylene glycol methacrylate (NPMA) group, and a third monomer having butyl methacrylate (BMA) group. A copolymer poly(MPC-co-BMA-co-NPMA) (PMBN) containing them is schematically expressed by the formula (2) below:

(Chemical Formula 5)

(2)

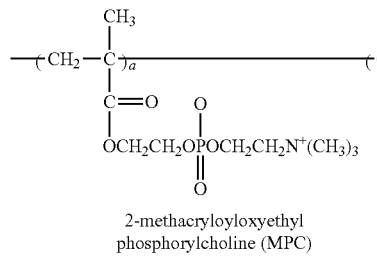
2-methacryloyloxyethyl phosphorylcholine (MPC)

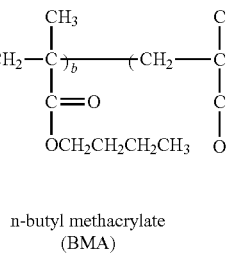
n-butyl methacrylate (BMA)

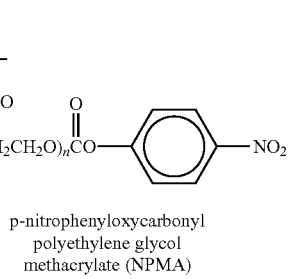
p-nitrophenyloxycarbonyl polyethylene glycol methacrylate (NPMA)

Where, in the formula (2), each of a, b and c independently represents a positive integer. In the formula (2), the first to third monomers may form a block copolymer, or these monomers may form a random copolymer.

Thus-configured copolymer expressed by the formula (2) is more excellently balanced among an appropriate degree of hydrophobicity, a property of suppressing non-specific adsorption of the template RNA fragment, and a property of immobilizing the primer. Therefore, by using such copolymer, the carrier may be covered with the polymer substance in a more reliable manner, and the primer may be introduced by immobilization through a covalent bond in a more reliable manner, while suppressing non-specific adsorption of the template RNA fragment to the carrier coated with the polymer substance.

The copolymer expressed by the formula (2) may be obtained by mixing the individual monomers of MPC, BMA, and NPMA, according to any publicly-known methods of polymerization such as radical polymerization. For the case where the copolymer expressed by the formula (2) is produced by radical polymerization, the polymerization may be proceeded by solution polymerization in an atmosphere of inert gas such as Ar, under temperature conditions of 30° C. or higher and 90° C. or lower.

The solvent used for solution polymerization may properly be selected, wherein alcohols such as methanol, ethanol and isopropanol, ethers such as diethyl ether, and organic solvents such as chloroform may be used in an independent or mixed manner. More specifically, a mixed solvent of diethyl ether and chloroform mixed at a ratio by volume of 8:2 may be used.

A radical polymerization initiator used for the radical polymerization reaction may be any of those generally used. For example, azo-base initiators such as azobisisobutyronitrile (AIBN) and azobisvaleronitrile; and oil-soluble organic peroxides such as lauroyl peroxide, benzoyl peroxide, t-butylperoxy neodecanoate, and t-butylperoxy pivalate may be used.

More specifically, the polymerization may be proceeded by using a mixed solvent of diethyl ether and chloroform mixed at a ratio by volume of 8:2 and AIBN, in Ar at 60° C. for 2 to 6 hours.

Although the polymer substance explained in this embodiment has the third unit containing a butyl methacrylate group, the first polymer substance may be defined as having the first unit containing a phosphorylcholine group and the second unit containing a group derived from carboxylic acid, and the second polymer substance having the first unit containing a phosphorylcholine group and the third unit containing a butyl methacrylate group may additionally be contained.

The first unit of the first polymer substance and the first unit of the second polymer substance may have the same structure, or may have different structures. If the first polymer substance contains the third unit containing a butyl methacrylate group, the third unit of this first polymer substance and the third unit of the second polymer substance may have the same structure, or may have different structures.

Thus-configured second polymer substance may be used as a polymer suppressing non-specific adsorption of the template DNA fragment. As this sort of polymer, MPC polymer (from NOF Corporation) having 30 mol % of phosphorylcholine group and 70 mol % of butyl methacrylate group, may typically be used.

If the polymer substance is composed of the first polymer substance and the second polymer substance, these polymer substances may be mixed. Since the polymers of the individual polymer substances are soluble, for example, to ethanol solution, the mixed polymer may readily be obtained by mixing the individual polymer solutions.

The carrier containing, in the surficial portion thereof, a coating layer composed of the above-described polymer substance may be obtained by coating a liquid containing the polymer substance onto the surface of the carrier being processed as having a predetermined shape, followed by drying. Alternatively, the carrier may be immersed into a liquid containing the polymer substance, and then dried.

The carrier configured by using a plastic material may be preferable in view of ensuring flexibility to modification in the shape and size, and provision at lower prices as compared with glass carrier. This sort of plastic material preferably has a glass transition point of 100° C. or higher, and may more preferably be composed of thermoplastic resin, from the viewpoint of readiness in surface treatment and mass productivity.

The thermoplastic resin may be a low phosphorescence emission substrate. By using the resin of a low phosphorescence emission, the background level in detection reaction of DNA chains may be lowered, and thereby the detection sensitivity may further be improved. The thermoplastic resin of a low phosphorescence emission adoptable herein may be exemplified by straight-chain polyolefins such as polyethylene and polypropylene;
cyclic polyolefins; and
fluorine-containing resins.

Of these resins, saturated cyclic polyolefins are particularly excellent in heat resistance, chemical resistance, low phosphorescence emission, transparency and moldability, therefore suitable for optical analysis, and are preferably used as a material for composing the carrier.

The saturated cyclic polyolefins herein mean saturated polymers obtained by hydrogenating homopolymer having cyclic olefin structure, or copolymer of cyclic olefin and α-olefin. Examples of the former include saturated polymers produced by hydrogen addition of polymers obtained by ring-opening polymerization of norbornene-base monomer represented by norbornene, dicyclopentadiene and tetracyclododecene, or these alkyl substituted products thereof. The latter copolymers are saturated polymers produced by hydrogenating random copolymer of α-olefins such as ethylene, propylene, isopropylene, 1-butene, 3-methyl-1-butene, 1-pentene, 3-methyl-1-pentene, 1-hexene and 1-octene with cyclic olefin monomer. Of the copolymers, those co-polymerized with ethylene are most preferable. These resins may be used independently, or may be used in a form of copolymer or mixture of two or more species. Not only the saturated cyclic polyolefins obtained by ring-opening polymerization of monomers having cyclic olefin structures, but also saturated cyclic polyolefins obtained by addition polymerization of monomers having cyclic olefin structures may be used.

The carrier containing, in the surficial portion thereof, the above-described polymer substance may be obtained by coating a liquid containing the polymer substance onto the surface of the carrier being processed as having a predetermined geometry, followed by drying. Alternatively, the carrier may be immersed into a liquid containing the polymer substance, and then dried.

The carrier composed of plastics may readily be processed in a form of microtiter plate represented by those of 96-well type and 384-well type, in a form of substrate represented by slide glass, in a form of bead, in a form of sheet and so forth, wherein those in a form of microtiter plate represented by those of 96-well type and 384-well type may be preferable for the case where liquid phase reaction is involved.

The polynucleotide for DNA elongation immobilized to the insoluble carrier is used as a primer, and as described later, those having at least one sequence complementary to the poly-A tail of the mRNA, and at least one RNA promoter are preferably used.

Next, the polynucleotide for DNA elongation is immobilized on the surface of the carrier. Paragraphs below will explain a specific example of the method of immobilization.

(i) A polynucleotide is immobilized onto the surface of the carrier, by allowing at least a part of activated ester group, out of a plurality of activated ester groups contained in the polymer substance on the carrier, to react with polynucleotide, to thereby form a covalent bond, and then (ii) the activated ester groups on the surface of the carrier, other than those having the polynucleotide immobilized thereto, or in other words, the residual activated ester groups may be inactivated. The individual process steps will be explained below.

In the step (i), for the case where the shape of the carrier is substrate-like, immobilization of the polynucleotide to be annealed with the template RNA fragment may preferably be carried out by a method of spotting a liquid having the polynucleotide dissolved or dispersed therein.

For the case where the shape of the carrier has a form of microtiter plate, a liquid having the polynucleotide dissolved or dispersed therein is dispensed.

A part of the activated ester groups contained in the polymer substance react with the polynucleotide, to thereby form covalent bonds with the polynucleotide.

The liquid having the polynucleotide dissolved or dispersed therein may be adjusted to neutral to alkaline, and typically to pH7.6 or above.

After immobilization of the polynucleotide, a portion of the polynucleotide remained unimmobilized onto the surface of the carrier may be washed off using pure water or buffer.

As shown in the step (ii), after the washing, the activated ester groups on the surface of the carrier, other than those having the polynucleotide immobilized thereto, are inactivated using an alkaline compound, or a compound having a primary amino group.

The alkaline compounds adoptable herein include sodium hydroxide, potassium hydroxide, sodium carbonate, sodium hydrogen carbonate, disodium hydrogenphosphate, calcium hydroxide, magnesium hydroxide, sodium borate, lithium hydroxide, potassium phosphate and so forth.

The compounds having a primary amino group adoptable herein include glycine, 9-aminoaquadine, aminobutanol, 4-aminobutyric acid, aminocaprylic acid, aminoethanol, 5-amino-2,3-dihydro-1,4-pentanol, aminoethanethiol hydrochloride, aminoethanethiol sulfate, 2-(2-aminoethylamino) ethanol, 2-aminoethyl dihydrogenphosphate, aminoethyl hydrogensulfate, 4-(2-aminoethyl)morpholine, 5-aminofluorescein, 6-aminohexanoic acid, aminohexyl cellulose, p-aminohippuric acid, 2-amino-2-hydroxymethyl-1,3-propanediol, 5-aminoisophthalic acid, aminomethane, aminophenol, 2-aminooctane, 2-aminooctanoic acid, 1-amino-2-propanol, 3-amino-1-propanol, 3-aminopropene, 3-aminopropionitrile, aminopyridine, 11-aminoundecanoic acid, aminosalicylic acid, aminoquinoline, 4-aminophthalonitrile, 3-aminophthalimide, p-aminopropiophenone, aminophenyl acetic acid, aminonaphthalene. Of these, the aminoethanol and glycine are preferably used.

The polynucleotide to be immobilized onto the carrier preferably has an amino group preliminarily introduced thereinto, in view of enhancing reactivity with the activated ester group. The amino group is excellent in reactivity with the activated ester group, so that the polynucleotide having the amino group introduced thereinto may be immobilized onto the surface of the carrier in an effective and strong manner. Position of introduction of amino group may be on the terminal of the molecular chain of the polynucleotide, or may be on the side chain, wherein introduction on the terminal of the molecular chain may be preferable, in view of allowing annealing with a complementary template RNA fragment to proceed in a more efficient manner.

By these procedures, an array having the polynucleotide immobilized on the surface of the carrier may be obtained. After immobilization of the single-strand cDNA in this way, and removal of the liquid phase, the single-strand cDNA-immobilized carrier may be obtained.

Next, (2) a solution containing RNA fragments, nucleotide monomers, and a reverse transcriptase or an enzyme having polymerase activity is brought into contact with the surface of the insoluble carrier.

More specifically, a sample containing the template RNA fragment for DNA elongation to be annealed with the polynucleotide for DNA elongation immobilized onto the surface of the insoluble carrier, nucleotide monomers containing dATP, dCTP, dGTP and dTTP (any one of which may be labeled), and a reverse transcriptase or an enzyme showing polymerase activity, is introduced.

In the reaction of thus-introduced sample, elongation reaction using the RNA template is allowed to proceed with the aid of a reverse transcriptase and/or an enzyme having polymerase activity, wherein the reverse transcriptase and/or the enzyme having polymerase activity applicable to the present invention includes Moloney murine leukemia virus (M-MLV) reverse transcriptase, Rous sarcoma virus (RSV) reverse transcriptase, avian myeloblastosis (AMV) reverse transcriptase, Rous-associated virus (RAV) reverse transcriptase, myeloblastosis-associated virus (MAV) reverse transcriptase, human immunodeficiency virus (HIV) reverse transcriptase, retrovirus reverse transcriptase, retrotransposon reverse transcriptase, hepatitis B reverse transcriptase, cauliflower mosaic reverse transcriptase, bacterial reverse transcriptase, *Thermus thermophilus* (Tth) DNA polymerase, *Thermus aquaticus* (Taq) DNA polymerase, *Thermotoga neopolitana* (Tne) DNA polymerase, *Thermotoga maritime* (Tma) DNA polymerase, *Thermococcus litoralis* (Tli, for example, VENT (registered trademark) brand) DNA polymerase, *Pyrococcus furiosus* (Pfu) DNA polymerase, *Pyrococcus* species GBD (for example, DEEPVENT™ brand) DNA polymerase, *Pyrococcus woosii* (Pwo) DNA polymerase, *Bacillus sterothermophilus* (Bst) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus rubber* (Tru) DNA polymerase, *Thermus brockianus* (for example, DYNAZYME (registered trademark) brand) DNA polymerase, *Methanobacterium thermoautotrohicum* (Mth) DNA polymerase, variant, modified product and derivatives thereof, but are not limited thereto.

It is more better to add an RNase inhibitor, for the purpose of suppressing decomposition of the template RNA.

Next, (3) the polynucleotide for DNA elongation immobilized onto the surface of the carrier is allowed to elongate, using the RNA fragment in the solution as a template to form a single strand cDNA.

More specifically, by controlling temperature of the above-described reaction system, the elongation reaction of DNA chain proceeds, or more specifically, a DNA fragment complementary to the template RNA fragment is formed on the carrier, and thereby a cDNA chain as being hybridized with the RNA chain may be obtained.

There are no special limitations on the reaction temperature and reaction time, allowing appropriate setting of reaction conditions, depending on characteristics of the DNA polymerase, restriction enzymes and so forth, and stability, quality and absolute content of the template DNA or RNA.

After completion of the elongation reaction, washing is carried out typically using a 0.1 wt % SDS solution, to thereby terminate the reaction for forming cDNA.

As has been described in the above, the present invention provides a method of synthesizing a DNA chain in a liquid phase, by using the above-described, single-strand DNA-immobilized carrier, which includes bringing a solution containing the sense and antisense primers, the DNA polymerase, and the nucleotide monomers into contact with the carrier, and allowing PCR to proceed under a predetermined heat cycle, to thereby elongate and amplify the DNA chain using the single-strand DNA immobilized onto the carrier as a template.

Second Embodiment

The present invention provides also a method of synthesizing a cDNA chain using an insoluble carrier having on the surface thereof a polymer substance containing a first unit having a group derived from a phosphoric ester composing the hydrophilic portion of phospholipid, and a second unit having a group derived from carboxylic acid having an electron-attractive substituent bound to a carbonyl group, which includes:

(a) allowing at least one polynucleotide for DNA elongation, containing a sequence complementary to the poly-A tail of an mRNA, to bind to the insoluble carrier;

(b) adding a sample solution containing an mRNA having the poly-A tail, a solution containing a reverse transcriptase, and a solution containing nucleotide monomers, to the carrier having immobilized thereon the nucleotide for DNA elongation;

(c) allowing the poly-A tail of the mRNA to hybridize with the sequence complementary to the poly-A tail; and (d) allowing the polynucleotide for DNA elongation to elongate using the mRNA as a template, to thereby form an antisense cDNA complementary to the mRNA.

In step (a), the insoluble carrier may be same as that explained in the first embodiment. The polynucleotide for DNA elongation adoptable herein may be such as containing a sequence complementary to the poly-A tail of the mRNA, and more preferably, may further contain at least one RNA promoter. Binding of the polynucleotide onto the insoluble carrier may be proceeded similarly to as described in the first embodiment.

The polynucleotide to be immobilized onto the carrier in the present invention preferably contains at least one sequence complementary to the poly-A tail of the mRNA. The polynucleotide-immobilized carrier is also versatile for various methods including synthesis of sense or antisense cDNA. The polynucleotide-immobilized carrier is still also useful for synthesis of sense or antisense mRNA.

The polynucleotide to be immobilized onto the carrier in the present invention preferably contains a sequence, for example oligo-dT, complementary to the poly-A tail of the mRNA. Moreover, it is also preferable to contain a promoter sequence of mRNA.

From another point of view, the present invention provides also a nucleotide-immobilized insoluble carrier having, as being immobilized on an insoluble carrier, a polynucleotide containing at least one sequence complementary to the poly-A tail of an mRNA, the insoluble carrier having on the surface thereof a polymer substance containing a first unit having a group derived from a phosphoric ester composing the hydrophilic portion of phospholipid, and a second unit having a group derived from carboxylic acid having an electron-attractive substituent bound to a carbonyl group. The immobilized nucleotide further contains at least one, more preferably at least two, RNA promoters.

The polynucleotide is generally immobilized onto an insoluble plate, such as microtiter plate, and the present invention provide such microtiter plate.

A microtiter plate according to another preferable embodiment of the present invention has at least two wells, having different polynucleotides respectively immobilized therein. The polynucleotide-immobilized carrier of the present invention may be used for synthesizing sense or antisense single-strand cDNA, and sense or antisense mRNA. The single-strand cDNA synthesized on the polynucleotide-immobilized carrier of the present invention is stable over a long period, and immobilized on the surface of substrate in a stable manner, allowing use in production of cDNA or mRNA, under a large number of times of repetition.

In one preferable embodiment of the present invention, the polynucleotide containing at least one sequence complementary to the poly-A tail of RNA is immobilized onto the insoluble carrier, to thereby configure a nucleotide-immobilized carrier. These sequences preferably have a length of 6 to 100 nucleotides. In more preferable embodiment, the immobilized polynucleotide further contains an RNA promoter, and/or restriction enzyme recognition site. More preferably the 5'-terminal thereof is immobilized to the insoluble carrier, and the 3'-terminal thereof is complementary to the poly-A tail of the mRNA.

One embodiment of the present invention relates to a polynucleotide-immobilized carrier having, on an insoluble plate, which is preferably a microtiter plate, a polynucleotide immobilized thereon. The immobilized polynucleotide contains at least one sequence, for example poly-dT, complementary to the poly-A tail of the mRNA.

In a more preferable embodiment, the immobilized polynucleotide has an RNA promoter. Another embodiment of the present invention relates to a polynucleotide-immobilized carrier, preferably having a polynucleotide bound to the insoluble carrier containing at least one RNA promoter. A most preferable embodiment relates to the polynucleotide containing either of T7 or SP6 RNA promoter.

Still another embodiment of the present invention has an insoluble carrier, and preferably a single-strand DNA-immobilized carrier composed of the insoluble carrier and a single-strand DNA bound thereto, wherein the single-strand DNA at least contains a sequence complementary to the poly-A tail of the mRNA. In a preferable embodiment of the present invention, the single-strand DNA has an RNA promoter, and more preferably, the single-strand DNA contains at least two different RNA promoters. Most preferably, these promoters are T7 or SP6 RNA promoter.

Next, in step (b), a sample solution containing mRNA having the poly-A tail is added to the carrier having the polynucleotide for DNA elongation immobilized thereto, and a solution containing a reverse transcriptase, and a solution containing nucleotide monomers containing dATP, dCTP, dGTP and dTTP (any one of which may be labeled) are added thereto.

In step (c), the poly-A tail of the mRNA is hybridized with the sequence, complementary to the poly-A tail, of the polynucleotide for DNA elongation immobilized onto the carrier. In step (d), the polynucleotide for DNA elongation is elongated using mRNA as a template, to thereby obtain a cDNA chain complementary to the mRNA. Steps (c) and (d) may be allowed to proceed in the same liquid phase, and each of steps (c) and (d) may involve incubation at a predetermined temperature, typically at 37° C.

More specifically, the second embodiment is to provide a method of synthesizing a single-strand cDNA-immobilized carrier, by which a polynucleotide, more preferably a polynucleotide having at least one RNA promoter, is bound to the insoluble carrier. The polynucleotide preferably has at least one sequence complementary to the poly-A tail of mRNA, and forms the nucleotide-immobilized carrier. A solution containing mRNA having the poly-A tail, such as cell solubilized solution, is added thereto, to thereby hybridize the polyadenylic acid tail (poly-A tail) of the mRNA with the immobilized polynucleotide sequence, and more preferably the carrier and the solution are incubated. An antisense cDNA complementary to the annealed mRNA is thus synthesized.

Alternatively, a double-strand cDNA chain may be synthesized by bringing a solution containing a DNA polymerase, a DNA ligase and nucleotide monomers into contact with the surface of a cDNA-immobilized carrier additionally containing an RNA promoter, wherein the carrier being manufactured as having a single-strand cDNA immobilized thereon as described in the above, followed by removal of the liquid phase, and such method of synthesizing a DNA chain may be provided by the present invention. In the method of synthesizing a DNA chain, the nucleotide monomers contained in the solution to be brought into contact with the single-strand cDNA-immobilized carrier may be exemplified by dATP, dCTP, dGTP and dTTP. For the case where the obtained double-strand cDNA is labeled, at least one of these nucleotide monomers used herein is preliminarily labeled.

Alternatively, a sense RNA chain may be synthesized by bringing a solution containing an RNA polymerase and nucleotide monomers into contact with the surface of a double-strand cDNA-immobilized carrier additionally containing an RNA promoter, wherein the carrier being manufactured as having a double-strand cDNA immobilized thereon as described in the above, followed by removal of the liquid phase, and such method of synthesizing a sense RNA chain may be provided by the present invention. In the method of synthesizing a RNA chain, the nucleotide monomers contained in the solution to be brought into contact with the double-strand cDNA-immobilized carrier may be exemplified by ATP, CTP, GTP and UTP. For the case where the obtained sense RNA is labeled, at least one of these nucleotide monomers used herein is preliminarily labeled.

When a sample solution containing reagents allowing the promoter to initiate transcription, an antisense mRNA is synthesized. In a preferable method of synthesizing the antisense mRNA, an initial liquid phase and a solid phase are produced by incubating the carrier and the sample solution, and the reaction is initiated according to the following steps:

(1) together with a reaction mixture containing an RNA polymerase, ATP, CTP, GTP and UTP, preferably a reaction mixture containing one of labeled NTPs is added to the solid phase, wherein the mixture contains ATP, CTP, GTP and UTP as the nucleotide monomers, at least one of which being labeled; and (2) the liquid phase and the reaction mixture are incubated, and the solid phase and reaction mixture are then heated, to thereby produce a liquid phase containing the antisense mRNA.

It is preferable to collect the liquid phase thereafter, and treat it with DNase, so as to allow the reaction to continue.

As has been described in the above, from another point of view, the present invention provides also a method of synthesizing an RNA chain, by bringing a solution containing a DNA polymerase, a DNA ligase, and nucleotide monomers into contact with the surface of a single-strand cDNA-immobilized carrier additionally containing an RNA promoter, wherein the carrier being manufactured as having a single-strand cDNA immobilized thereon as described in the above, followed by removal of the liquid phase, to thereby synthesize an antisense mRNA from the RNA promoter.

The present invention provides also a method of synthesizing a sense single-strand cDNA, by synthesizing a double-strand cDNA as described below, and then heating a second reaction mixture with the solid phase. In this process, a second liquid phase containing the sense single-strand cDNA may be obtained.

(1) To the polynucleotide-immobilized carrier, a sample solution containing mRNA having the poly-A tail is added.

(2) The sample solution and the carrier are incubated, to thereby produce a first liquid phase and a solid phase.

(3) A first reaction mixture, containing a reverse transcriptase and nucleotide monomers (dATP, dCTP, dGTP, dTTP, and labeled nucleotide (dNTP)) are added to the solid phase.

(4) A second reaction mixture containing RNase, DNA polymerase, DNA ligase, dATP, dCTP, dGTP and dTTP is added to the solid phase.

(5) The second reaction mixture and the solid phase are incubated.

From still another point of view, the present invention provides also a method of synthesizing a sense cDNA, using the double-strand cDNA-immobilized carrier described in the above. After the sense cDNA and the antisense cDNA form the double-strand cDNA in the liquid phase, the double-strand cDNA is unfolded, and the sense cDNA may be obtained in the liquid phase.

One of the features of the embodiment of the present invention resides in a method of synthesizing sense single-strand cDNA. This method involves production of the double-strand cDNA-immobilized carrier in the liquid phase, wherein one chain of the double-strand DNA chain is immobilized to the insoluble carrier, whereas the other chain of the double-strand cDNA contains at least one sequence complementary to the poly-A tail of mRNA. Thereafter, the double-strand cDNA-immobilized carrier is unfolded, and thereby the sense cDNA is obtained in the liquid phase.

In the present invention, the sense mRNA means an mRNA equivalent to genetic information, whereas the antisense mRNA means a polynucleotide complementary to the sense mRNA. The sense single-strand cDNA contains genetic information equivalent to that of the sense mRNA. Exceptions are that, in the cDNA, uracil in the mRNA is replaced with thymine, and that nucleotides are deoxyribonucleotides, rather than ribonucleotide.

EXAMPLES

Manufacture of PNBM-Coated 96-Well Microtiter Plate

A 96-well microtiter plate was molded by injection molding, using a hydrogenated product of a ring-opened polymer of 5-methyl-2-norbornene (MFR: 21 g/10 min, ratio of hydrogenation: substantially 100%, thermal deformation temperature: 123° C.). The individual wells were coated with a 0.5 wt % ethanol solution of 2-methacryloyloxyethyl phosphorylcholine-butyl methacrylate-p-nitrophenyloxycarbonyl polyethylene glycol methacrylate copolymer (PNBM: ratio of the individual groups is 25:74:1 on the mol % basis), and the bottom surface of the mold product was coated with PNBM, to thereby manufacture a PNBM-coated, 96-well microtiter plate according to one embodiment of the present invention. The plate will be referred to as "PNBM plate", hereinafter.
(Manufacture of Aldehyde-Group-Modified, 96-Well Microtiter Plate)

A 96-well microtiter plate was molded by injection molding, using a hydrogenated product of a ring-opened polymer of 5-methyl-2-norbornene (MFR: 21 g/10 min, ratio of hydrogenation: substantially 100%, thermal deformation temperature: 123° C.). The molded 96-well titer plate is treated by an oxygen plasma, amino groups were introduced using aminosilane, and aldehyde groups were then introduced onto the amino groups using glutaraldehyde, to thereby manufacture an aldehyde-group-modified 96-well microtiter plate. The plate will be referred to as "aldehyde plate", hereinafter.
(Immobilization of Oligo-T)

Each of three kinds of oligo-T (T15, T20, T30) respectively having sequences shown below, and each having the 5'-terminal modified with an amino group, was dissolved into a 0.25 M carbonate buffer (pH9.0), to thereby obtain a 10 μM oligo-T solution. Ten microliters of each oligo-T solution was then dispensed into the individual wells of the PNBM plate and the aldehyde plate, the bottom surface of each well was covered with a piece of ETFE sheet punched into a 5-mm circle, and the plate was allowed to stand at 80° C. for 1 hour. The ETFE sheet was removed from each well, and the plate was washed. After the washing, the individual wells were blocked. For the PNBM plate, 400 μl of a 1 mol/l NaOH solution, used as a blocking solution, was dispensed in each well, and the plate was allowed to stand at room temperature of 5 minutes. Thereafter the blocking solution was removed, and the plate was washed with pure water. For the aldehyde plate, a blocking solution was prepared by dissolving 0.6 g of sodium borohydride and 50 ml of ethanol into 180 ml of a phosphate buffer, 400 μl of thus-prepared blocking solution was dispensed into each well, the plate was allowed to stand at room temperature for 5 minutes, the blocking solution was removed, and the plate was washed with pure water.

The individual plates were dried, and subjected to experiments of synthesizing cDNA from a total RNA, described in the next.

| oligo-T | sequence |
|---------|----------|
| T15 | TTTTTTTTTTTTTTT (sequence No. 1) |
| T20 | TTTTTTTTTTTTTTTTTTTT (sequence No. 2) |
| T30 | TTTTTTTTTTTTTTTTTTTTTTTTTTTTTT (sequence No. 3) |

(Synthesis of cDNA Chain from Total mRNA)

One hundred microliters of aqueous DEPC treatment solution containing 1 μg of human liver total RNA (derived from normal human liver tissue: CB-061009, from Cosmo Bio Co., Ltd.) was kept at 65° C. for 5 minutes, and quenched on ice. A reaction liquid was prepared by adding reverse transcriptase M-MLV (RNase H-), 5× reverse transcriptase M-MLV buffer, RNase inhibitor (Super), 1 mM Cy3-labeled dUTP, 20 mM dATP, 20 mM dGTP, 20 mM dCTP, and DEPC treated water, and the liquid was added to a human liver total RNA solution. Five microliters of the solution was dispensed into each well, each well was covered with a 5-mm-diameter ETFE sheet from the top, followed by incubation at 42° C. for 1 hour. After the incubation, 200 μl of TE buffer (10 mM Tris/HCl (pH8.5), 1 mM EDTA) was dispensed to each well, to thereby floate the ETFE sheet for removal. The plate was washed twice using the TE buffer, then washed with pure water, and dried.

A phosphorescence image of the bottom surface of each well was taken under a phosphorescence microscope, intensity of phosphorescence was expressed by numerical value by image processing, and states of cDNA syntheses were compared. Observation of phosphorescence means that cDNA was synthesized, wherein larger phosphorescence intensity means more efficient synthesis of cDNA.

Values of phosphorescence intensity of the individual wells of the PNBM plate and the aldehyde plate immobilized with each oligo-T were shown in Table 1. Values of phosphorescence intensity of the individual wells were expressed as net values obtained by subtracting values of phosphorescence intensity observed for the wells having no oligo-T immobilized therein.

TABLE 1

| | Plate | |
|---------|-----------|----------------|
| Oligo-T | PNBM plate | Aldehyde plate |
| T15 | 687 | 28 |
| T20 | 1376 | 35 |
| T30 | 2654 | 63 |

Elongation of the cDNA chain was detected on the PNBM plate as one embodiment of the present invention, whereas no elongation of the cDNA chain was detected on the aldehyde plate.

A specific embodiment of the present invention will be given below.

A method of synthesizing a cDNA chain using an insoluble carrier having on the surface thereof a polymer substance containing a first unit having a group derived from a phosphoric ester composing the hydrophilic portion of phospholipid, and a second unit having a group derived from carboxylic acid having an electron-attractive substituent bound to a carbonyl group, which includes:

(a) allowing at least one polynucleotide for DNA elongation, containing a sequence complementary to the poly-A tail of an mRNA, to bind to the insoluble carrier;

(b) adding a sample solution containing an mRNA having the poly-A tail to the carrier having immobilized thereon the nucleotide for DNA elongation;

(c) adding a solution containing a reverse transcriptase to the solution containing mRNA having the poly-A tail;

(d) adding a solution containing nucleotide monomers to the solution containing mRNA having the poly-A tail;

(e) allowing the poly-A tail of the mRNA to hybridize with the sequence complementary to the poly-A tail; and (f) allowing the polynucleotide for DNA elongation to elongate using the mRNA as a template, to thereby form an antisense cDNA complementary to the mRNA.

[Sequence Table]
SB-90030.ST25.txt (a) allowing at least one polynucleotide for DNA elongation, containing a sequence complementary to the poly-A tail of an mRNA, to bind to said insoluble carrier, wherein the polynucleotide has an amino group;

(b) adding a sample solution containing an mRNA having the poly-A tail, a solution containing a reverse transcriptase, and a solution containing nucleotide monomers, to said carrier having immobilized thereon the nucleotide for DNA elongation to thereby form a liquid phase containing said carrier;

(c) allowing said poly-A tail of the mRNA to hybridize with the sequence complementary to the poly-A tail in said liquid phase obtained in step (b); and (d) allowing the polynucleotide for DNA elongation to elongate using the mRNA as a template, to thereby form an antisense cDNA complementary to the mRNA in said liquid phase obtained in step (b), wherein said polynucleotide for DNA elongation is immobilized onto the surface of the carrier via a covalent bond formed by the reaction of the amino group of the polynucleotide with the p-nitrophenyloxycarbonyl group of the NPMA contained in the copolymer with leaving of the p-nitrophenyloxy group of the p-nitrophenyloxycarbonyl group.

The invention claimed is:

1. A method of synthesizing a cDNA chain using an insoluble carrier having on the surface thereof a copolymer composed of a first monomer having a 2-methacryloyloxyethyl phosphorylcholine (MPC) group, a second monomer having p-nitrophenyloxycarbonyl polyethylene glycol methacrylate (NPMA) group and a third monomer having a butyl methacrylate (BMA) group, comprising:

2. The method of synthesizing a cDNA chain as claimed in claim 1,
wherein each of steps (c) and (d) involves incubation at a predetermined temperature.

3. The method of synthesizing a cDNA chain as claimed in claim 1,
wherein the group derived from a phosphoric ester contained in the first unit of said polymer substance is at least any one species selected from phosphorylcholine group, phosphoryl ethanolamine group, phosphoryl serine group, phosphoryl inositol group, phosphoryl glycerol group, and phosphatidyl phosphoryl glycerol group.

4. The method of synthesizing a cDNA chain as claimed in claim 1,
wherein said solution containing nucleotide monomers contains dATP, dCTP, dGTP and dTTP.

5. The method of synthesizing a cDNA chain as claimed in claim 1,
wherein said polynucleotide for DNA elongation further contains at least one RNA promoter.

6. A method of synthesizing a DNA chain comprising bringing a solution containing a DNA polymerase, a DNA ligase and nucleotide monomers into contact with the surface of a cDNA-immobilized carrier additionally containing an RNA promoter, said carrier being manufactured as having a single-strand cDNA immobilized thereon by the method of synthesizing a cDNA chain described in claim 5, followed by removal of the liquid phase to form a double-strand cDNA chain.

7. The method of synthesizing a DNA chain as claimed in claim 6,
wherein said nucleotide monomers contain dATP, dCTP, dGTP and dTTP, at least one of which being labeled.

8. A method of synthesizing a sense RNA chain comprising bringing a solution containing an RNA polymerase and nucleotide monomers into contact with the surface of a double-strand cDNA-immobilized carrier additionally containing an RNA promoter, said carrier being manufactured as having a double-strand cDNA immobilized thereon by the method of synthesizing a DNA chain described in claim 6, and then followed by removal of the liquid phase, to synthesize an RNA chain.

9. The method of synthesizing a sense RNA chain as claimed in claim 8,
wherein said nucleotide monomers contain ATP, CTP, GTP and UTP, at least one of which being labeled.

* * * * *

```
                    SEQUENCE LISTING

<160> NUMBER OF SEQ ID NOS: 3

<210> SEQ ID NO 1
<211> LENGTH: 15
<212> TYPE: DNA
<213> ORGANISM: Artificial
<220> FEATURE:
<223> OTHER INFORMATION: Designed DNA probe for synthesis for DNA

<400> SEQUENCE: 1
tttttttttt ttttt                                                   15

<210> SEQ ID NO 2
<211> LENGTH: 20
<212> TYPE: DNA
<213> ORGANISM: Artificial
<220> FEATURE:
<223> OTHER INFORMATION: Designed DNA probe for synthesis for DNA

<400> SEQUENCE: 2
tttttttttt tttttttttt                                              20

<210> SEQ ID NO 3
<211> LENGTH: 30
<212> TYPE: DNA
<213> ORGANISM: Artificial
<220> FEATURE:
<223> OTHER INFORMATION: Designed DNA probe for synthesis for DNA

<400> SEQUENCE: 3
tttttttttt tttttttttt tttttttttt                                   30
```